United States Patent [19]
Smith

[11] Patent Number: 4,947,858
[45] Date of Patent: Aug. 14, 1990

[54] METHOD AND APPARATUS FOR DATA COMPRESSION IN AN ECG MONITORING SYSTEM

[75] Inventor: Nancy C. Smith, McMinnville, Oreg.

[73] Assignee: Hewlett-Packard Company, Palo Alto, Calif.

[21] Appl. No.: 305,258

[22] Filed: Jan. 31, 1989

[51] Int. Cl.⁵ ............................................. A61B 5/04
[52] U.S. Cl. ................................. 128/696; 128/708
[58] Field of Search ............... 128/696, 708, 710, 711, 128/712, 703, 704; 364/413.06

[56] References Cited

U.S. PATENT DOCUMENTS

| | | | |
|---|---|---|---|
| 4,449,536 | 5/1984 | Weaver | 128/696 |
| 4,567,883 | 2/1986 | Langer et al. | 128/696 |
| 4,721,114 | 1/1988 | DuFault et al. | 128/696 |

OTHER PUBLICATIONS

"ECG Data Compression Using Fourier Descriptors", Reddy et al., IEEE Transactions on Biomedical Engineering, vol. BNE-33, No. 4, Apr. 1986, pp. 428-434.
"Data Compression for Storing and Transmitting ECG's/VCG's", Womble et al., Proceedings of the IEEE, vol. 65, No. 5, May 1977.
A Method for the Construction of Minimum Redundancy Codes, D. A. Huffman.
A Universal Algorithm for Sequential Data Compression—Jacob Ziv.
Aztec, A Preprocessing Program Developed for Real Time ECG Rhythm Analysis—G. C. Oliver, Jr.
Scan-along Polygonal Approximation for Data Compression of Electrocardiograms—M. Ishijima et al.
Arrhythmia Detection Program for an Ambulatory ECG Monitor—W. C. Mueller.

Primary Examiner—Lee S. Cohen
Assistant Examiner—Scott Getzow
Attorney, Agent, or Firm—S. A. Kassatly

[57] ABSTRACT

A method and apparatus for data compression of input ECG beats in an electro-cardiograph system. The data compression method includes the steps of conditioning the analog input ECG beats into filtered digital data; identifying the individual QRS peaks in the beats; and compressing the beats. The step of compressing a beat includes selectively sub-sampling the beat; template matching and differencing the beat with a template beat, namely the immediately preceding beat of its type (normal, ectopic or artifact); and coding the sub-sampled differenced beat. The step of selective sub-sampling includes dividing the QRS region into at least two subregions centered about the QRS peak; and selectively sub-sampling each sub-region at a different compression ratio.

15 Claims, 6 Drawing Sheets

METHOD AND APPARATUS FOR DATA COMPRESSION IN AN ECG MONITORING SYSTEM

BACKGROUND OF THE INVENTION

1. Field of the Invention

The present invention relates in general to cardiac monitoring systems, and it more particularly relates to an inventive method and apparatus for data compression in an electro-cardiograph (ECG) monitoring system.

2. Background Information

ECG monitoring systems, such as the portable real-time solid-state Holter monitors, have inherent limitaions in the memory capacity for storing ECG data. These limitations are generally due to constraints on the power consumption and size of the portable monitor, as well as the increased cost of an enlarged memory capacity.

Such limitations render data compression of the ECG signal almost mandatory. However, data compression may require substantial processing time, and may introduce significant distortion.

Several conventional methods for the compression of ECG data have attempted to compensate for the rate of data compression and signal distortion caused thereby. These methods can be classified in two general categories. The first category covers the noiseless or non-distorting compression; and the second category covers the irreversible or distoring compression.

The non-distorting compression mode causes the data or signal to be compressed in such a way that the original data can be reconstructed from the compressed data without losing information. Such non-distorting compression modes are exemplified by the Huffman coding method and the Lempel-Ziv method, as described respectively in the following articles: Huffman, D. A. A method for the construction of minimum-redundancy codes, *Proc. IEEE* 40: 1098–1101. 1952; and Ziv, J. and Lempel, A. A universal algorithm for sequential data compression, *IEEE Trans. Inform. Theory* IT-23 pp. 337–343. 1977.

Due to the limitations in the memory capacity of the portable ECG monitoring system, the non-distorting ECG compression method by itself does not generally provide sufficient compression to store a full day (24 hours) of ECG data in the designated memory. Wherefore, distorting compression methods have been used to compensate for the limited memory capacity at the expense of the overall fidelity of the ECG monitoring system.

The distorting compression methods result in the of loss of some of the original ECG information. These methods are exemplified by the AZTEC preprocessing software program, and the SAPA or fan method, as respectively described in the following articles: Cox, J. R., Nolle, F. M., Fozzard, H. A., and Oliver, G. C. Jr. AZTEC, a pre-processing program for real-time ECG rythm analysis, *IEEE Trans. Biomed. Eng.* BME-15 pp. 128–129. 1968; and Ishijima, M., Shin, S. B., Hostetter, G. and Sklansky, J. Scan-along polygonal approximation for data compression of electrocardiograms, *IEEE Trans. Biomed. Eng.* BME-26 pp. 723–729. 1983.

The AZTEC algorithm has been used to store ECG data for automatic analysis functions such as QRS detection, but it has proven to be generally inadequate for a visual presentation of the data. The SAPA or fan compression method, on the other hand, uses a straight line approximation of the waveform to store the ECG data. This method does not generally permit substantial data compression. Since the error threshold is uniform over the entire input waveform, the allowable error in the P- and T-wave region limits the overall compression.

Yet another exemplary distorting method is the Mueller approach or turning point algorithm, as described in Mueller, W. C. Arrhythmia detection program for an ambulatory ECG monitor, *Biomed. Sci. Instrum.* 14: 81–85. 1978. The turning point algorithm provides a compression factor of two (2) by selecting one of every set of two data points in the waveform. The second of the two data points is generally selected unless the first data point is a turning point, in which case the first point is selected. While this technique generally preserves the fidelity of the system at low compression rates, it has not proven to be adequate when extended to high compression factors.

Wherefore, it would be highly desirable to have a new and improved method and apparatus for data compression in an ECG monitoring system having limited memory capacity. Such compression method and apparatus should provide a sufficiently high compression factor as well as clinically acceptable results from the reconstructed data, and should not require excessive computer processing time.

SUMMARY OF THE INVENTION

It is therefore an object of the present invention to address the foregoing problems and to provide adequate solutions thereto.

Briefly, the above and further objects of the present invention are realized by a method and apparatus for data compression of input ECG beats in an electro-cardiograph system. The data compression method includes the steps of conditioning the analog input ECG beats into filtered digital data; identifying the individual QRS peaks in the beats; and compressing the beats.

The step of compressing a beat includes selectively sub-sampling the beat; template matching and differencing the beat with a template beat, namely the immediately preceding beat of its type (normal, ectopic or artifact); and coding the sub-sampled differenced beat.

The step of selective sub-sampling includes dividing the QRS region into at least two sub-regions centered about the QRS peak; and selectively sub-sampling each sub-region at a different compression ratio.

Therefore, the present ECG data compression apparatus and method present several distinctive advantages and features not offered by conventional ECG data compression techniques. The present ECG data compression technique is very efficient in that it requires a relatively small memory capacity, and short execution time. By filtering high frequency noise, and by reducing the baseline wander from the raw ECG data, the user obtains a better view of the actual ECG waveforms.

ECG monitoring systems such as real-time Holter monitor using the inventive method can compress and store ECG data over at least a twenty-four hour period in 1.5 Megabytes or less of memory.

The present data compression apparatus and method cause minimal distortion to the ECG data, which allows for a high quality printout in the miniaturized ECG format of a full disclosure report.

The variable or selective sampling technique requires that only one time value be saved. This is the number of data points between the regions of the different sampling ratios. Other conventional sampling techniques, such as the SAPA technique, require that time values be saved with every value, thus minimizing the compression capability of the ECG monitoring system.

BRIEF DESCRIPTION OF THE DRAWINGS

The above objects and features of the present invention, and the manner of attaining them will become apparent, and the invention itself will be better understood by reference to the following description of the embodiment of the invention taken in conjunction with the accompanying drawings, wherein.

DETAILED DESCRIPTION OF THE PREFERRED EMBODIMENT

Figure 1:
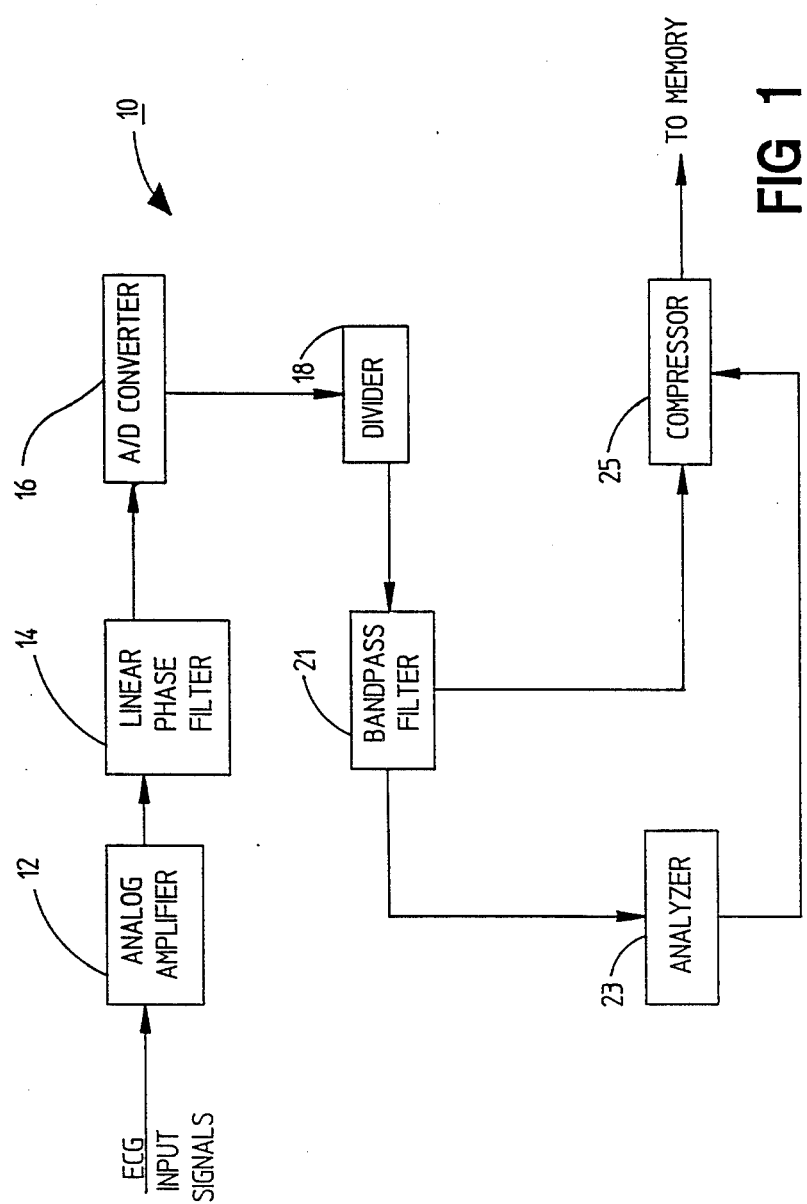
FIG. 1 is a block diagram of a data compression apparatus according to the present invention, for use in an ECG monitoring system.

Referring now to the drawings and more particularly to FIG. 1 thereof, there is illustrated a block diagram of a data compression apparatus 10 according to the present invention, for use in an ECG monitoring system. The data compression apparatus 10 generally comprises an analog amplifier 12 for receiving and amplifying input ECG data signals along one channel. It should however be understood that the inventive apparatus can process and compress input data along a plurality of channels.

A linear phase filter 14 filters the ECG signals at the output of the analog amplifier 12. An analog-to-digital converter 16 samples the digitized ECG data. It has been experimentally determined that certain applications of the present invention can be optimized by sampling a single channel of 11-bit-ECG data at 125 Hz and by limiting the slew rate to 8-bit first differences.

A divider 18 can be included to divide the ECG raw data at the output of the analog-to-digital converter 16, by a predetermined ratio, in order to reduce the data resolution to be compatible with the printer resolution. For example, a ratio of two which results in a least significant bit equivalent to 20 microvolts, has been found to be satisfactory for certain applications.

A bandpass filter 21, such as pseudo-matched FIR digital bandpass filter, is used to reduce high frequency noise and to limit the baseline wander of the ECG signals. The filtering process is therefore an important stage of the data conditioning. The ECG data can be divided by a predetermined ratio to further reduce its resolution to make it compatible with a given printer resolution.

A beat analyzer 23 receives the filtered data and determines the beat types and QRS times. A compressor 25 receives data from the analyzer 23 and the filter 21, and compresses the ECG signals in a new and inventive method 100, as it will be explained later in greater detail in connection with FIGS. 2 and 3.

Figure 2:
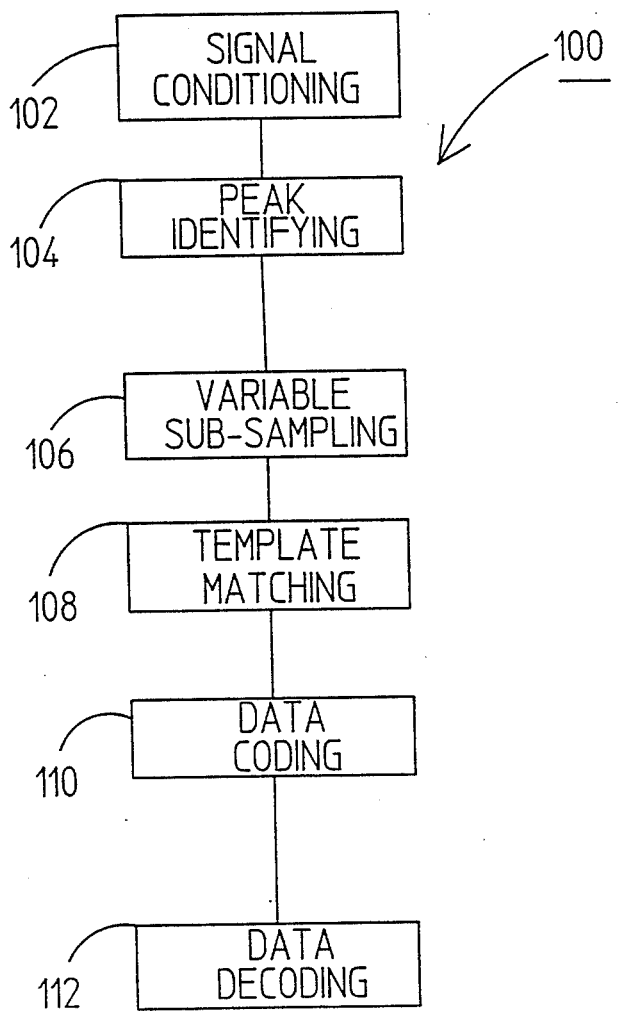
FIG. 2 is a block diagram illustrating a data compression method according to the present invention, for use in the data compression apparatus of FIG. 1.

In operation, the data compression apparatus 10 utilizes the inventive data compression method 100, as illustrated in FIG. 2. The raw input ECG signals are first conditioned at 102 by the analog amplifier 12, the filter 14, the analog-to-digital converter 16, the divider 18, and the bandpass filter 21, as described above in connection with FIG. 1.

QRS peak time information from the analyzer 23 is then used to identify the QRS peak at 104, and to sub-sample the ECG data at 106. Upon identification of the QRS peaks, the QRS peak times are used to divide the ECG data into individual beat units and to variably sub-sample and save different amounts of data in different regions of the ECG waveform.

The sub-sampling step 106 constitutes an important stage of the compression process. The QRS region is first divided into two or more sub-regions centered about the QRS peak. Each sub-region is then sub-sampled at a different ratio, wherefore this step is herein referred to as variable or selective sub-sampling.

It has been experimentally found that specific sub-sampling ratios for certain applications produce optimal results. For example, a 128 millisecond region (as indicated by the arrow A in FIG. 4) centered about the high frequency QRS region can be sampled at a ratio of 1 to 2, using the Mueller approach, i.e. the turning point algorithm.

The remaining region, (as indicated by the arrow B in FIG. 4) which is of lower frequency is sampled less frequently. A variation of the turning point algorithm can be used, such that the data is sampled at a ratio of 1 to 8, using the turning point algorithm three consecutive times in succession on each eight samples of data. Frequently, the times of the chosen samples are not saved with the amplitude values, thus causing a relatively slight temporal shift of the waveform peaks. Nonetheless, such distortion is generally imperceptible on a miniaturized ECG data full disclosure report.

All subsequent steps of the compression method 100 are preferably non-distorting processes. In the preferred embodiment, a template matching step is applied at 108, in order to partially code the beats that are made available by the analyzer 23. The QRS peak for each beat is lined up with the QRS peak of its template beat and differences in signals are then calculated.

The template for each beat is the previous beat of its type. For instance, a normal beat is matched and differenced with the previous normal beat; and an ectopic beat is matched and differenced with the previous ectopic beat. Thus, each beat becomes the template for the next beat of its type.

The rationale behind this beat differencing method is that if the ECG waveform varies slowly over time, then the best match to the current beat is most probably the template beat. The beat data resulting from the differencing technique typically has lower entropy than the beats before they are differenced. This renders the subsequent coding method more efficient.

The differenced beats are coded at 110. One such coding method uses a modified version of the Huffman coding procedure described in the following article: Cox, J. R. and Ripley, K. L. Compact digital coding of electrocardiograhic data, *Proceedings of the Sixth Hawaii International Conference of System Science* pp. 333–336. Honolulu, Hawaii: 1967. The resulting bit stream is then packeted into bytes and stored in the solid-state memory, for subsequent decoding at 112.

Figure 3:
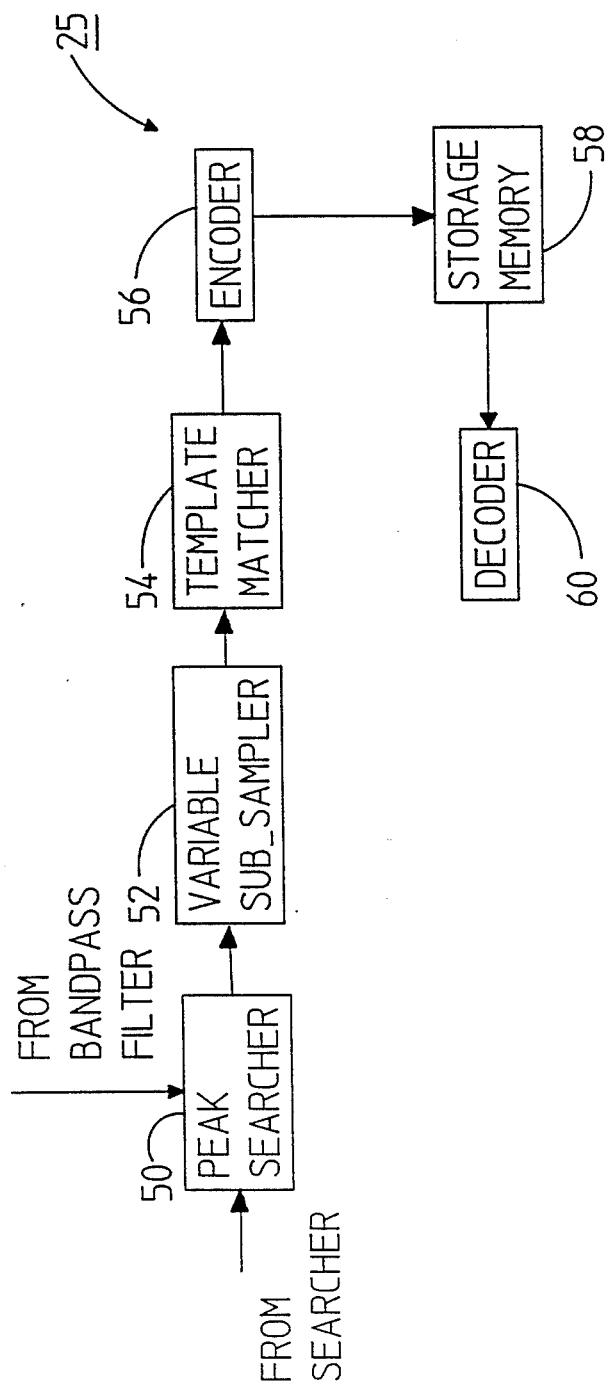
FIG. 3 illustrates a compressor used in the data compression apparatus of FIG. 1, using the compression method of FIG. 2.

Considering now the compressor 25 in greater detail with respect to FIG. 3, it generally includes a peak searcher 50 which receives the QRS peak time information from the real-time analyzer 23. Given the approximate location of each QRS peak, the analyzer searches for the absolute maximum peak amplitude.

A variable or selective sub-sampler 52 receives the peak information from the peak searcher 50, and selectively samples the data, as explained above in connection with step 106 of the data compression process 100.

A template matcher 54 partially codes the beats available from the sub-sampler 52, and compares the beats of the same types with their corresponding template beats, as described above in connection with step 108 of the compression process 100.

An encoder 56 utilizes the Huffman or other similar coding techniques to code the differenced beats, thus producing the compressed ECG data. Such data is then stored in a memory 58 for subsequent or further analysis. A decoder 60 decodes the compressed data, and reconstructs the original ECG signals using reverse decoding techniques, as those used in compressing the data.

While the analog amplifier 12, the linear phase filter 14, the analog-to-digital converter 16, the divider 18, the bandpass filter 21, the beat analyzer 23, the decoder 60 and the compressor 25 including the peak searcher 50, the variable sub-sampler 52, the template matcher 54, and the encoder 56 have been described above as comprising distinct hardware components, it should be understood that equivalent functions to those performed by these elements can be substantially performed by software programming.

Figure 4:
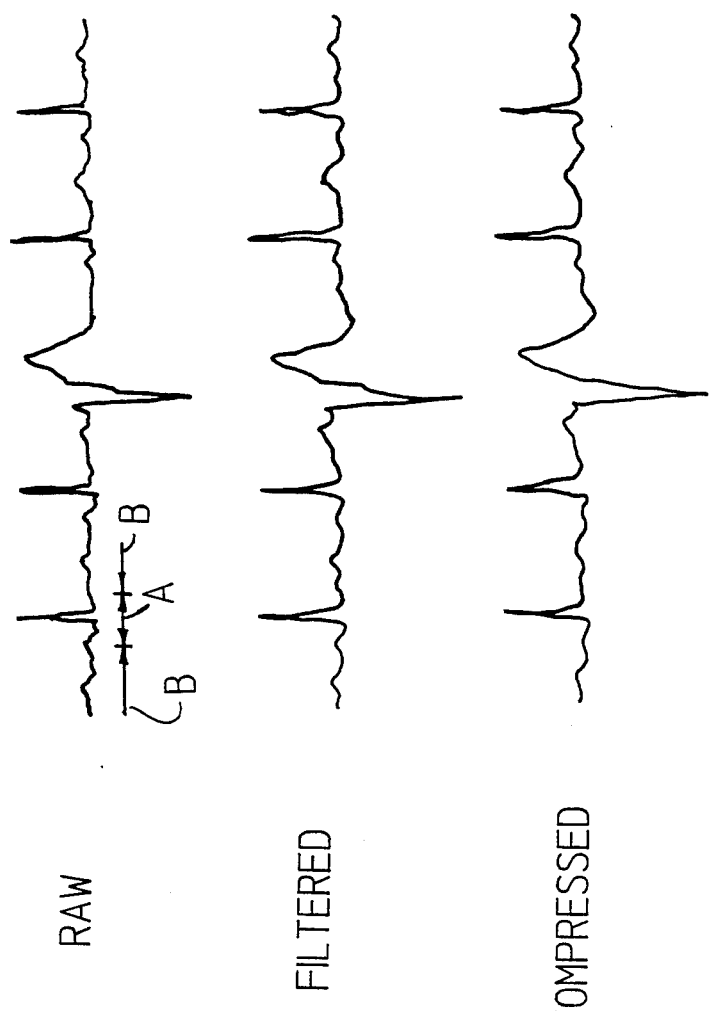
FIG. 4 illustrates comparative charts of raw, filtered and reconstructed ECG signals, showing normal and ectopic beats, wherein the reconstructed ECG signals were compressed by the data compression apparatus of FIG. 1.
Figure 5:
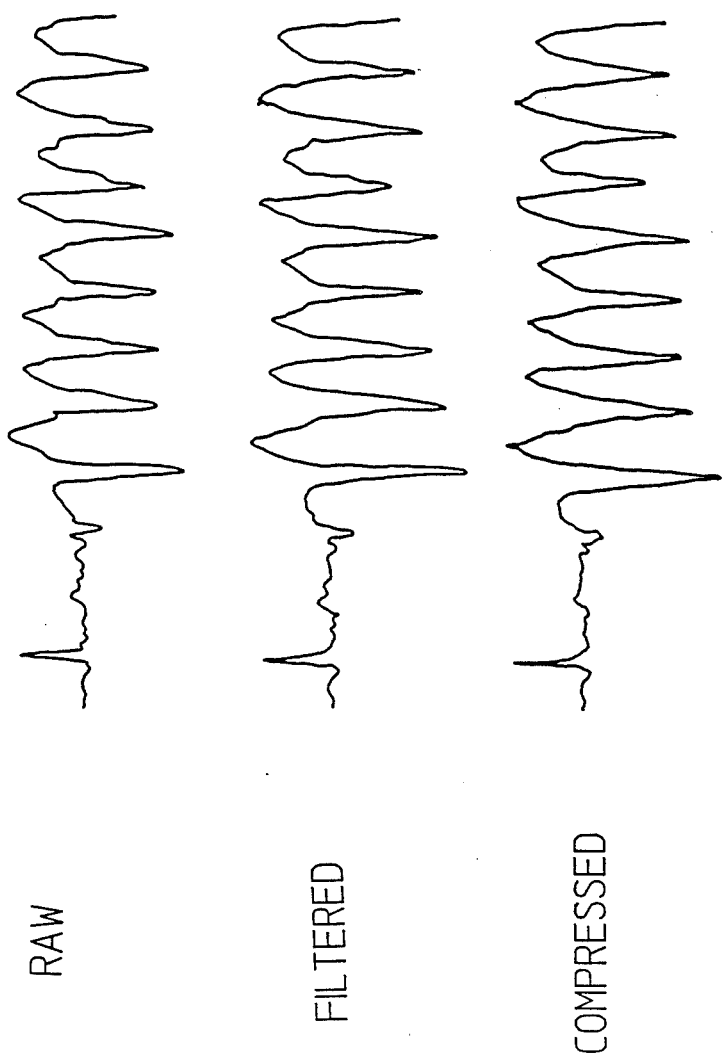
FIG. 5 illustrates comparative charts of raw, filtered and reconstructed ECG signals, showing normal and ectopic beats, wherein the reconstructed ECG signals were compressed by the data compression apparatus of FIG. 1.
Figure 6:
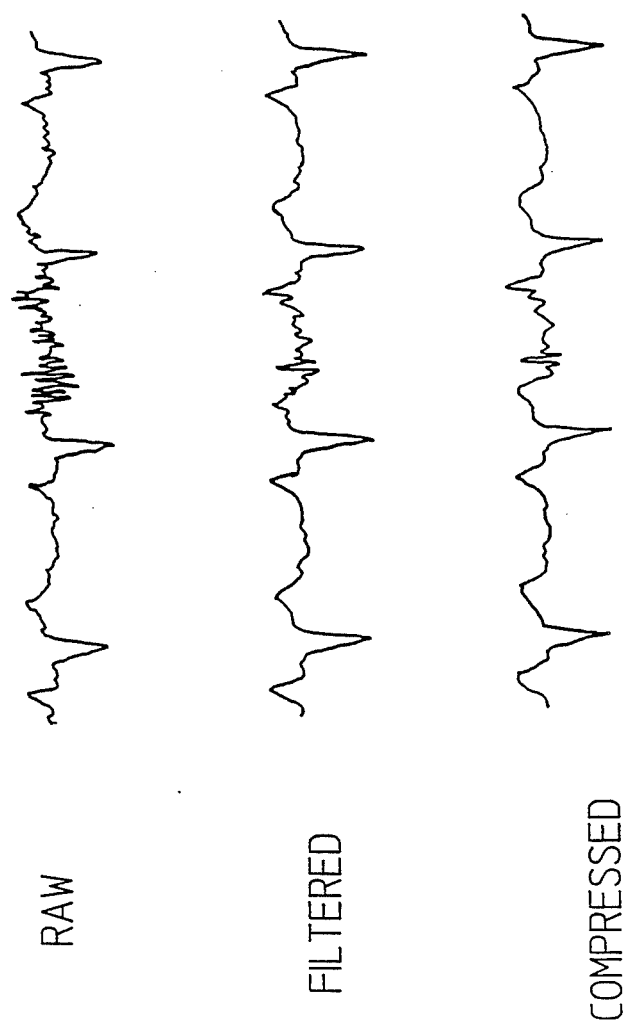
FIG. 6 illustrates comparative charts of raw, filtered and reconstructed ECG signals, showing normal and artifact beats, wherein said reconstructed ECG signals were compressed by the data compression apparatus of FIG. 1.

FIGS. 4, 5 and 6, illustrate a few exemplary experimental results in a real-time Holter monitoring system using the inventive data compression method. FIGS. 4 and 5 illustrate comparative charts of raw, filtered and compressed/reconstructed ECG signals, showing normal and ectopic beats. FIGS. 4 and 5 illustrate the fact that the present data compression method introduces minimal and clinically acceptable distortion.

FIG. 6 illustrates another comparative set of charts of raw, filtered and compressed/reconstructed ECG signals showing normal and artifact beats. FIG. 6 illustrates that the inventive data compression method generally enhances the ECG data by filtering undesirable high frequency noise.

Thus, as illustrated in FIGS. 4, 5 and 6, while the present data compression method and apparatus utilize relatively high compression ratios, i.e. 8 to 1 in certain regions of the ECG waveforms, the reconstructed waveforms are faithfully reproduced, in a clinically acceptable manner.

While a particular embodiment of the present invention has been disclosed, it is to be understood that various different modifications are possible and are contemplated within the true spirit of the appended claims.

There is no intention therefore, of limitations to the exact abstract or disclosure herein presented.

What is claimed is:

1. A method for compressing a sequence of input signals including analog ECG beats, comprising the steps of:
   (a) conditioning an input analog ECG beat into digital data by sampling and digitizing said input ECG beat;
   (b) identifying a QRS peak and a QRS region in said conditioned input ECG beat;
   (c) selectively sub-sampling said conditioned input ECG beat by
      (i) dividing said QRS region into a plurality of sub-regions, said sub-regions being generally centered about said QRS peak; and by
      (ii) selectively sub-sampling said sub-regions at different ratios; and
   (d) encoding a sub-sampled input beat.

2. The method as defined in claim 1, further including the steps:
   (a) matching said sub-sampled input beat with a template beat, said template beat comprising the beat of the same type as, and immediately preceding said conditioned input beat;
   (b) generating a difference signal relating to the difference between said sub-sampled input beat and its corresponding template beat; and
   (c) encoding said difference signal.

3. The method as defined in claim 2, further including the steps of storing said encoded signals; and reconstructing the sequence of input ECG signals by decoding said encoded signals.

4. The method as defined in claim 3, wherein said step of dividing said QRS region includes identifying at least two sub-regions centered about the QRS peak; and selectively sub-sampling each one of said sub-regions at a different ratio.

5. A method for compressing a sequence of input data including analog ECG beats comprising the steps of:
   (a) conditioning an input analog ECG beat into digital data by sampling and digitizing said input ECG beat;
   (b) identifying a QRS peak and a QRS region in said conditioned input ECG beat;
   (c) matching said conditioned input beat with a template beat, said template beat comprising the beat of the same type as, and immediately preceding said conditioned input beat;
   (d) generating a difference signal relating to the difference between said conditioned input beat and its corresponding template beat; and
   (e) encoding said difference signal.

6. An apparatus for compressing a sequence of input signals including ECG beats, the apparatus comprising:
   (a) means for conditioning an input ECG beat into digital data, said conditioning means including means for sampling and digitizing said input ECG beat;
   (b) means for identifying a QRS peak and a QRS region in said conditioned input ECG beat;
   (c) means for compressing the beat conditioned;
   (d) said compressing means including:
      (i) means for selectively sub-sampling said conditioned input ECG beat, said sub-sampling means including (1) means for dividing said QRS region of the conditioned beat into a plurality of sub-regions being generally centered about said QRS peak, and (2) means for selectively sub-sampling each of said sub-regions at different ratios;

(ii) means for matching said sub-sampled input beat with a template beat, said template beat including the beat of the same type as, and immediately preceding said conditioned input beat;

(iii) means for differencing the compressed conditioned beat with its corresponding template beat; and (iv) means for encoding a sub-sampled differenced beat.

7. The apparatus as defined in claim 6, wherein said means for encoding includes an encoder using the Huffman algorithm.

8. A method for compressing a sequence of input signals including analog ECG beats in an electro-cardiograph system, comprising the steps of:

(a) conditioning an input analog ECG beat into digital data by sampling and digitizing said input ECG beat;

(b) identifying an individual QRS peak and a QRS region in said conditioned input ECG beat;

(c) selectively sub-sampling said conditioned input ECG beat by (i) dividing said QRS region into two sub-regions, said sub-regions being generally centered about said QRS peak; and by (ii) selectively sub-sampling said sub-regions at different ratios;

(d) matching said conditioned input beat with a template beat, said template beat comprising the beat of the same type as, and immediately preceding said conditioned input beat;

(e) generating a difference signal relating to the difference between said conditioned input beat and its corresponding template beat;

(f) encoding said difference signal;

(g) storing said encoded difference signal;

(h) reconstructing the sequence of input ECG signals by decoding said encoded signals; and (i) said step of sub-sampling each one of said two sub-regions includes sampling a first high frequency central region at a ratio of 1 to 2, using the turning point approach.

9. The method as defined in claim 8, wherein said step of sub-sampling each one of the two sub-regions includes sampling a second lower frequency peripheral region at a ratio of 1 to 8 using the turning point approach.

10. The method as defined in claim 9, wherein said first high frequency central region is limited to about 128 milliseconds about the QRS peak.

11. A method for compressing a sequence of input signals including analog ECG beats, comprising the steps of:

(a) conditioning an input analog ECG beat into digital data by sampling and digitizing said input ECG beat;

(b) identifying a QRS peak and a QRS region in said conditioned input ECG beat;

(c) selectively sub-sampling said conditioned input ECG beat by (i) dividing said QRS region into at least two sub-regions, said sub-regions being generally centered about said QRS peak; and by (ii) sub-sampling said sub-regions at different ratios, wherein a first one of said sub-regions is sampled at a ratio of 1 to 2; and (d) encoding said sub-sampled input beat.

12. The method as defined in claim 11, wherein a second one of said sub-regions is sampled at a ratio of 1 to 8.

13. In an apparatus for compressing a sequence of input signals including analog ECG beats, comprising:

(a) means for conditioning an input analog ECG beat into digital data by sampling and digitizing said input ECG beat;

(b) means for identifying a QRS peak and a QRS region in said conditioned input ECG beat;

(c) means for selectively sub-sampling said conditioned input ECG beat, said sub-sampling means including (i) means for dividing said QRS region into two sub-regions, said sub-regions being generally centered about said QRS peak; and (ii) means for selectively sub-sampling said sub-regions at different ratios;

(d) means for matching a sub-sampled input beat with a template beat, said template beat comprising the beat of the same type as, and immediately preceding said conditioned input beat;

(e) means for generating a difference signal relating to the difference between said conditioned input beat and its corresponding template beat;

(f) means for encoding said difference signal;

(g) means for storing said encoded difference signal;

(h) means for reconstructing the sequence of input ECG signals including means for decoding said encoded signals; and (i) said means for sub-sampling each one of said two sub-regions includes means for sampling a first high frequency central region at a ratio of 1 to 2, using the turning point approach.

14. An apparatus for compressing a sequence of input signals including analog ECG beats, comprising:

(a) means for conditioning an input analog ECG beat into digital data by sampling and digitizing said input ECG beat;

(b) means for identifying a QRS peak and a QRS region in said conditioned input ECG beat;

(c) means for selectively sub-sampling said conditioned input ECG beat, said sub-sampling means including (i) means for dividing said QRS region into at least two sub-regions, said sub-regions being generally centered about said QRS peak; and (ii) means for sub-sampling said sub-regions at different ratios, wherein a first one of said sub-regions is sampled at a ratio of 1 to 2; and (d) means for encoding a sub-sampled input beat.

15. The apparatus as defined in claim 14, wherein a second one of said sub-regions is sampled at a ratio of 1 to 8.

* * * * *